US012702712B2

(12) United States Patent
Na et al.

(10) Patent No.: US 12,702,712 B2
(45) Date of Patent: Aug. 11, 2026

(54) ENTEROENDOCRINE CELL-TARGETING POLYMER SUBSTANCE CONJUGATED WITH PHOTOSENSITIZER, AND MEDICAL USE THEREOF FOR AMELIORATING METABOLIC DISEASE

(71) Applicant: The Catholic University of Korea Industry-Academic Cooperation Foundation, Seocho-gu (KR)

(72) Inventors: Kun Na, Bucheon-si Gyeonggi-do (KR); Sang Hee Lee, Bucheon-si Gyeonggi-do (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 773 days.

(21) Appl. No.: 17/926,496

(22) PCT Filed: Mar. 8, 2021

(86) PCT No.: PCT/KR2021/002830
§ 371 (c)(1),
(2) Date: Nov. 18, 2022

(87) PCT Pub. No.: WO2021/235661
PCT Pub. Date: Nov. 25, 2021

(65) Prior Publication Data

US 2023/0181737 A1 Jun. 15, 2023

(30) Foreign Application Priority Data

May 21, 2020 (KR) ........................ 10-2020-0060885

(51) Int. Cl.

| | |
|---|---|
| ***A61K 41/00*** | (2020.01) |
| ***A61K 47/54*** | (2017.01) |
| ***A61K 47/60*** | (2017.01) |
| ***A61K 47/61*** | (2017.01) |
| ***A61N 5/06*** | (2006.01) |
| ***A61P 3/04*** | (2006.01) |
| ***A61P 3/10*** | (2006.01) |

(52) U.S. Cl.
CPC ........ *A61K 41/0071* (2013.01); *A61K 47/542* (2017.08); *A61K 47/60* (2017.08); *A61K 47/61* (2017.08); *A61N 5/062* (2013.01); *A61P 3/04* (2018.01); *A61P 3/10* (2018.01)

(58) Field of Classification Search
CPC .. A61K 41/0071; A61K 47/542; A61K 47/59; A61K 47/60; A61K 47/61; A61P 3/00; A61P 3/04; A61P 3/10
See application file for complete search history.

(56) References Cited

U.S. PATENT DOCUMENTS

2005/0085455 A1* 4/2005 Chen ...................... A61N 5/062 604/20
2020/0297847 A1* 9/2020 Kim .......................... A61P 3/04

FOREIGN PATENT DOCUMENTS

KR 10-2014-0057718 A 5/2014
KR 101405403 B1 6/2014
KR 102112819 B1 5/2020

OTHER PUBLICATIONS

Lee et al., "Combined effect of oleic acid and polyethylene glycol 200 on buccal permeation of [D-Ala2, D-Leu5] enkephalin from a cubic phase of glyceryl monooleate," International Journal of Pharmaceutics 204, pp. 137-144 (2000).
Lee et al., "Lipid photosensitizers for suppression of gastric inhibitory polypeptide in obese with type 2 diabetes," Biomaterials 246, 119977 (2020).
Lee et al., "Oleic acid conjugated polymeric photosensitizer for metastatic cancer targeting in photodynamic therapy," Biomaterials Research, 24:1 (2020).
Li et al., "A novel chlorin-PEG-folate conjugate with higher water solubility, lower cytotoxicity, better tumor targeting and photodynamic activity," Journal of Photochemistry and Photobiology B: Biology, 127, pp. 28-37 (2013).
"Development of Technology to Eliminate Obesity and Diabetes with Only Light Exposure," Chosun Biz, Downloaded from web page: https://biz.chosun.com/site/data/html_dir/2020/04/13/2020041302979.html, Download date: May 21, 2020, original posting date: Apr. 13, 2020.
"Photodynamic therapy spurring the treatment of metabolic diseases such as obesity—Design of photoresponder to find cells that help fat accumulation," downloaded from web page: www.kidd.co.kr/news/215711, Download date: Aug. 19, 2021, original posting date: Apr. 18, 2020.
Int'l Search Report and Written Opinion issued Aug. 23, 2021 in Int'l Application No. PCT/KR2021/002830 (English translation of Int'l Search Report only).
Office Action issued May 13, 2022 in KR Application No. 10-2020-0060885.

* cited by examiner

*Primary Examiner* — Pancham Bakshi
(74) *Attorney, Agent, or Firm* — Panitch Schwarze Belisario & Nadel LLP

(57) ABSTRACT

A fatty acid-biocompatible polymer-photosensitizer conjugate is provided. The conjugate can kill GIP-secreting cells by generating active oxygen upon irradiation with light, and has the effect of increasing insulin, and thus can be effectively used for ameliorating and treating metabolic diseases such as obesity and diabetes.

5 Claims, 19 Drawing Sheets

[Fig. 1]
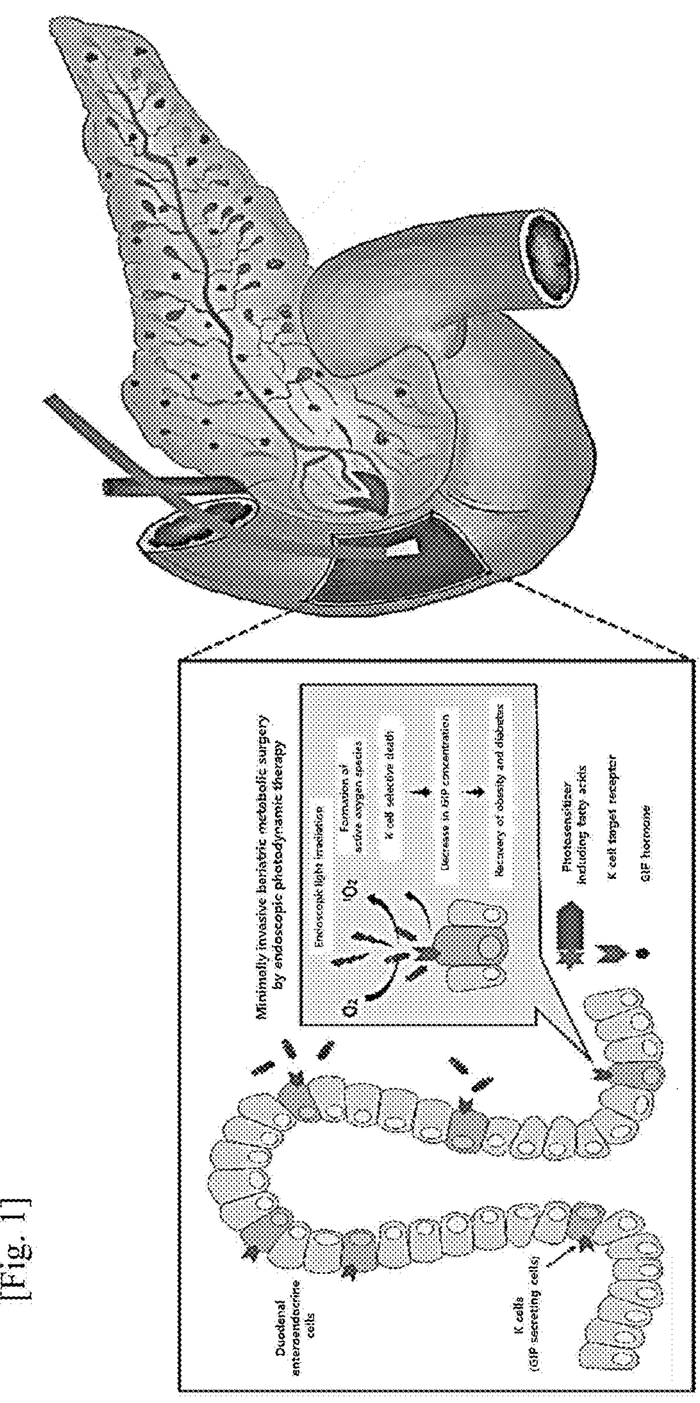

[Fig. 2]
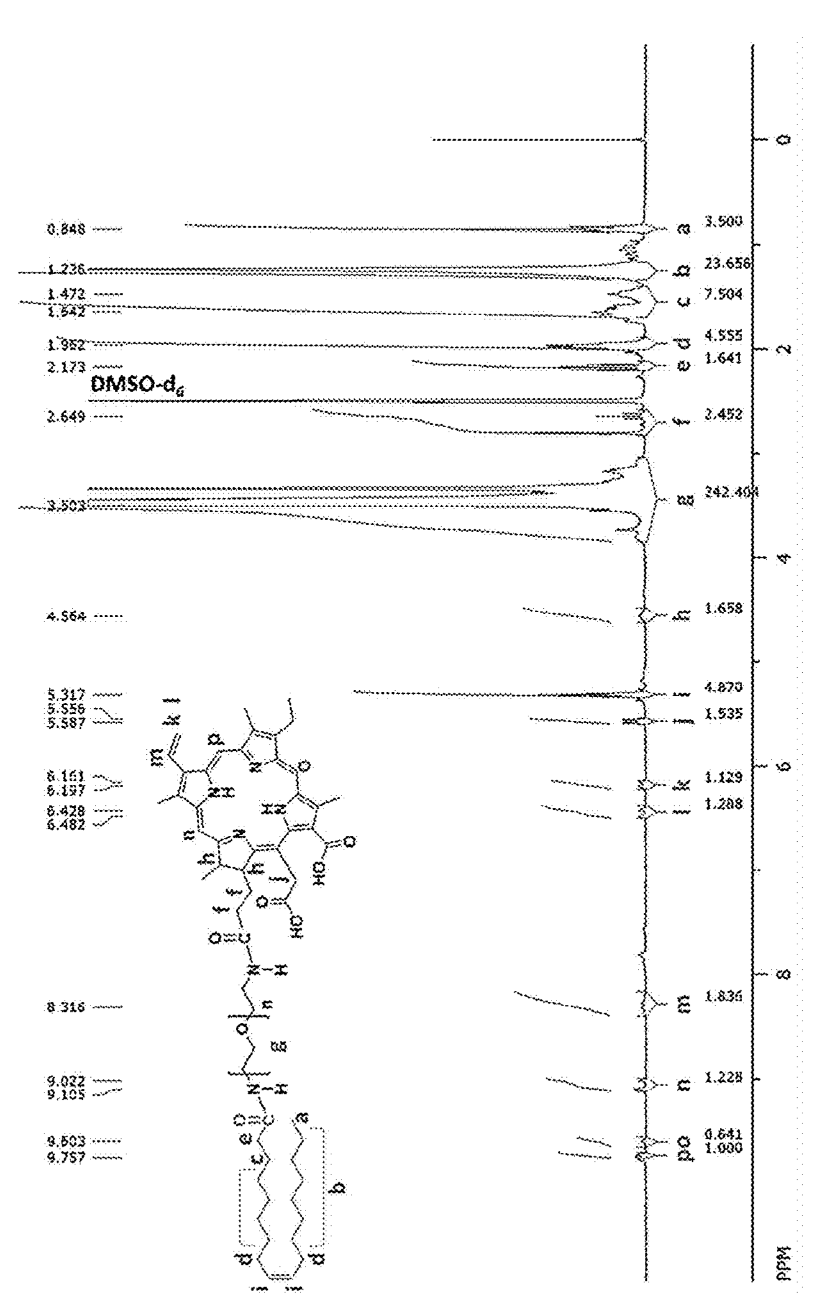

[Fig 3]
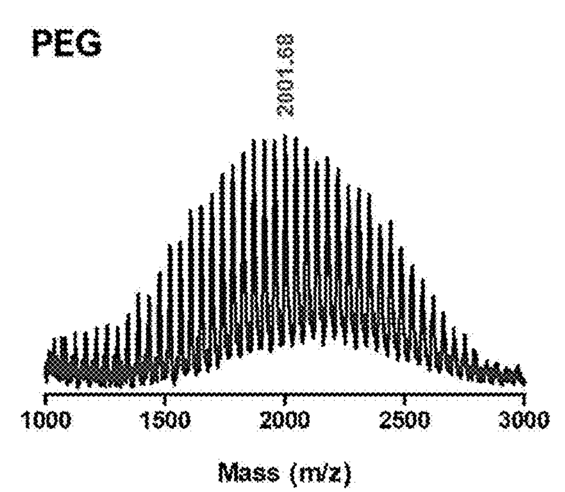
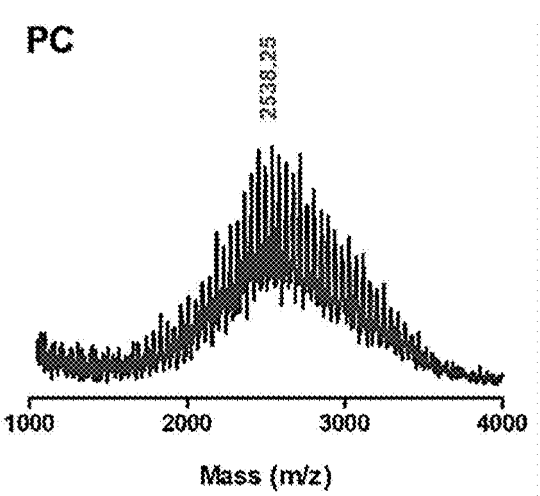
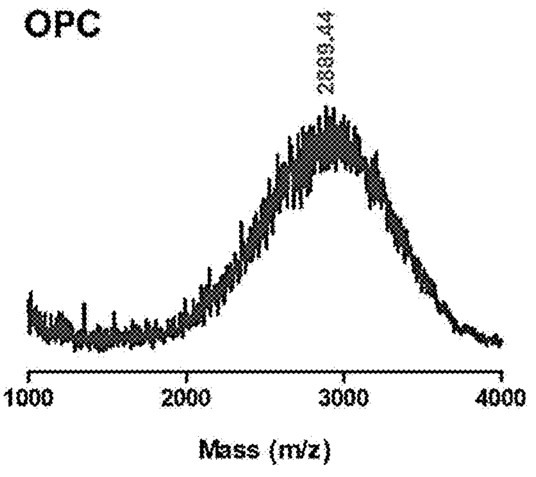

[Fig 6]
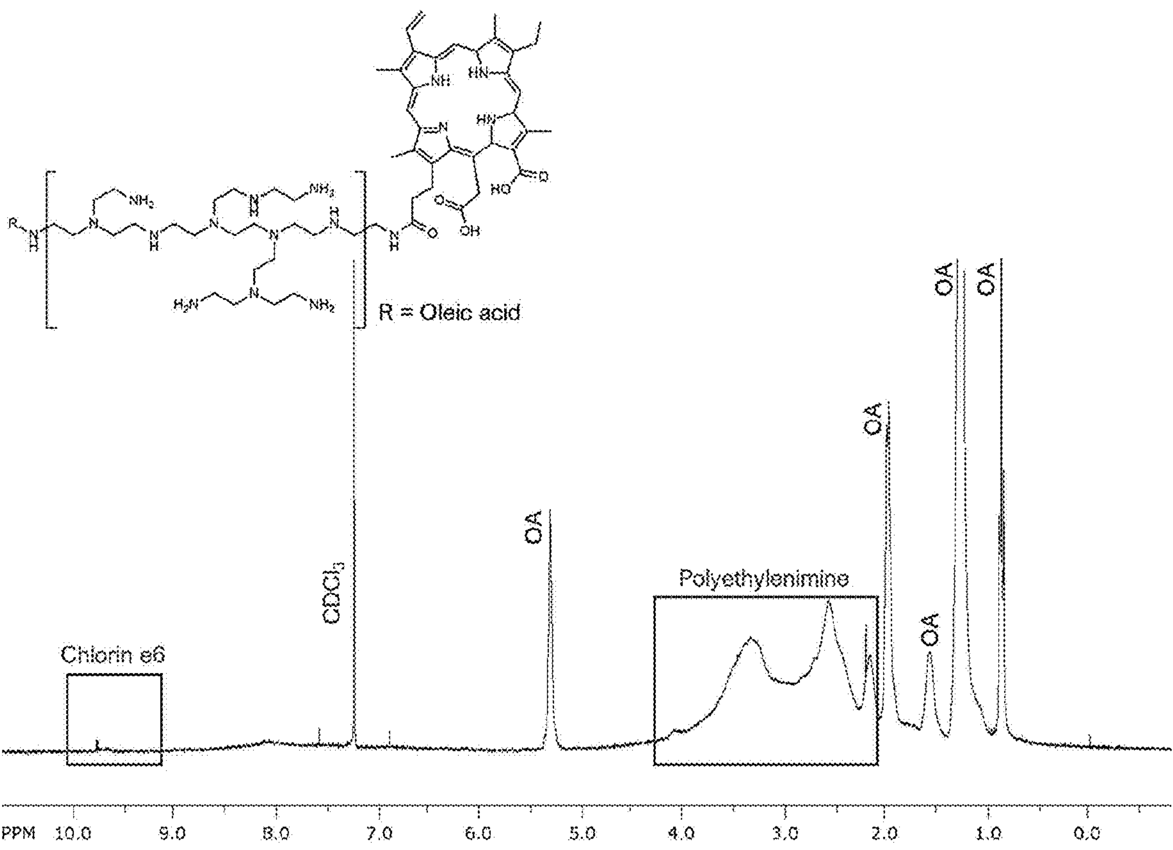

[Fig 7]
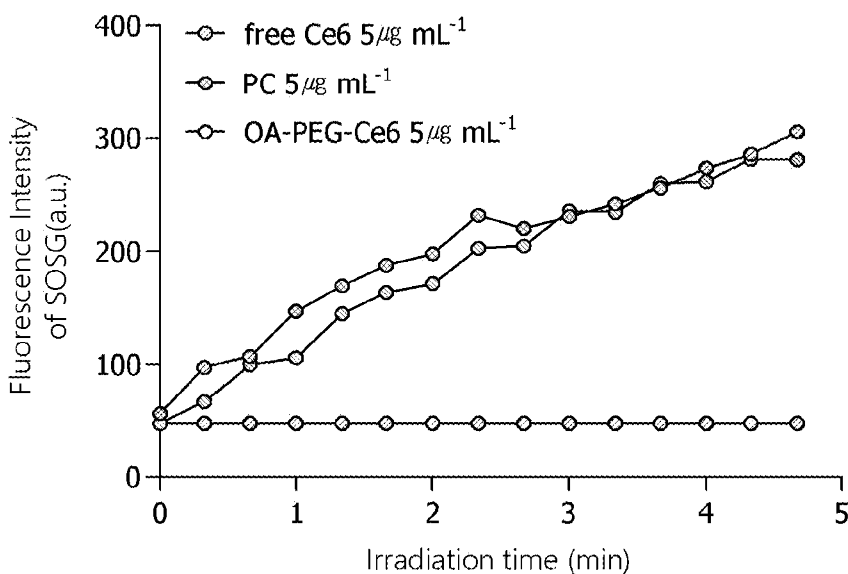

[Fig 8a]
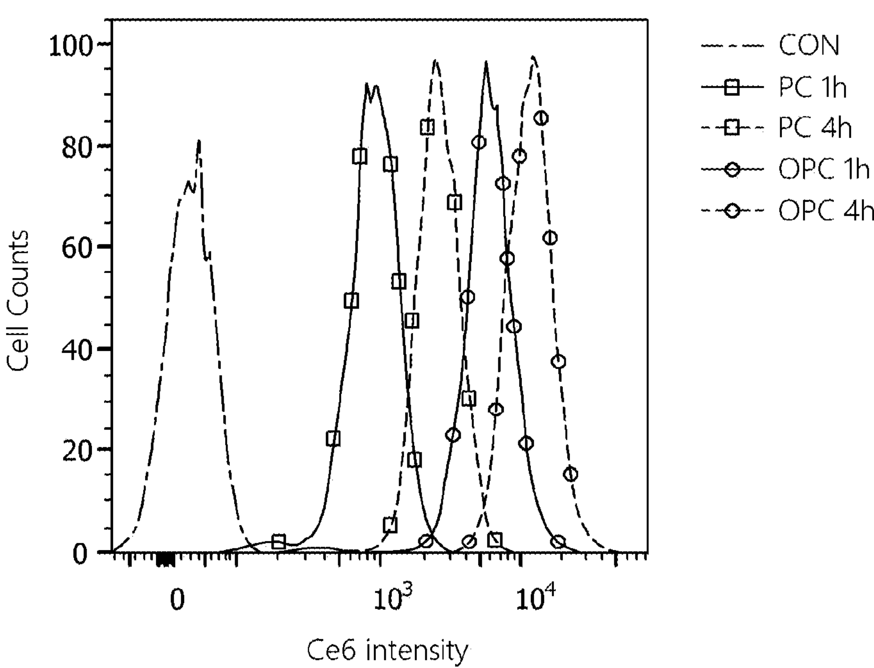

[Fig. 8b]
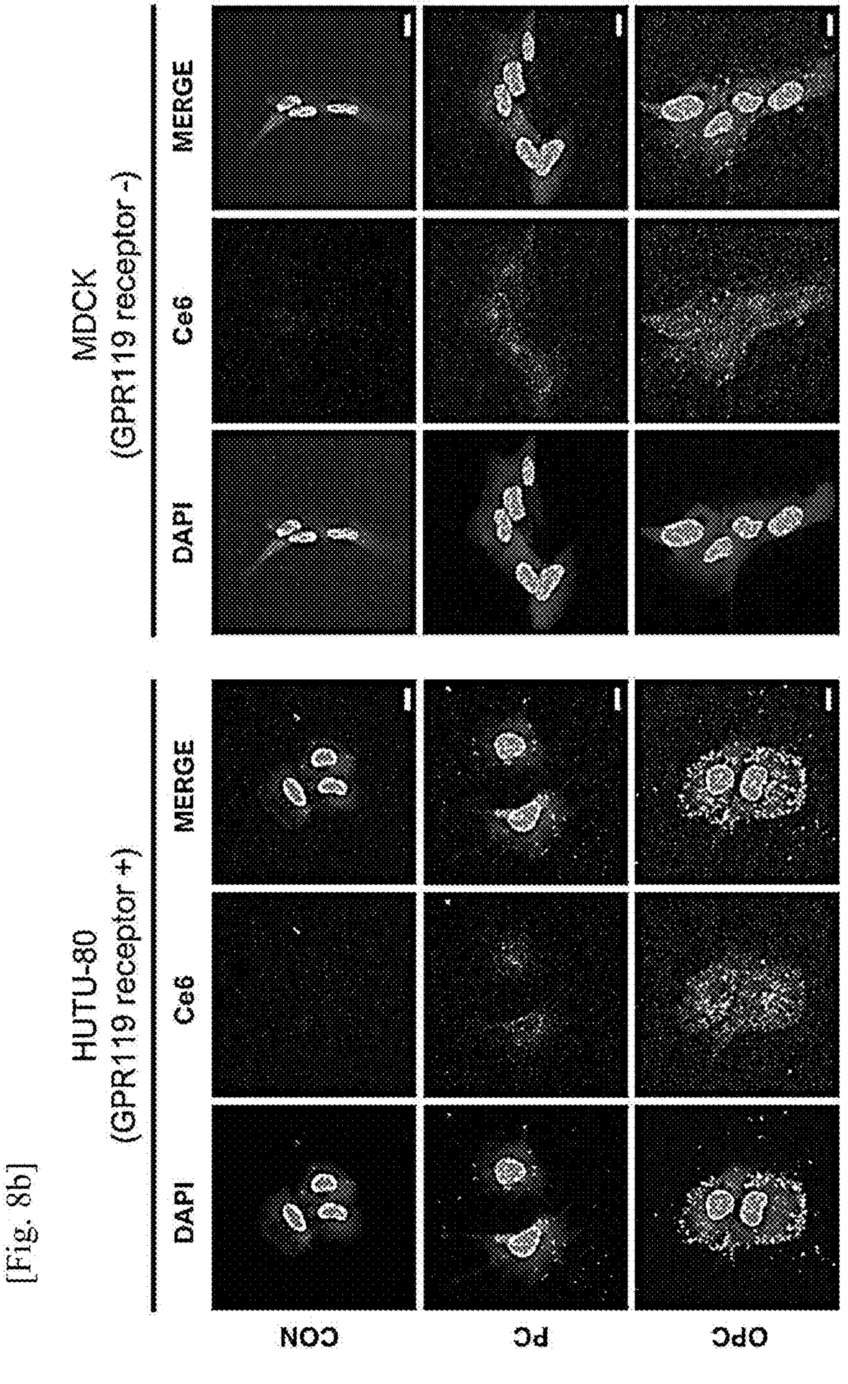

[Fig. 9]
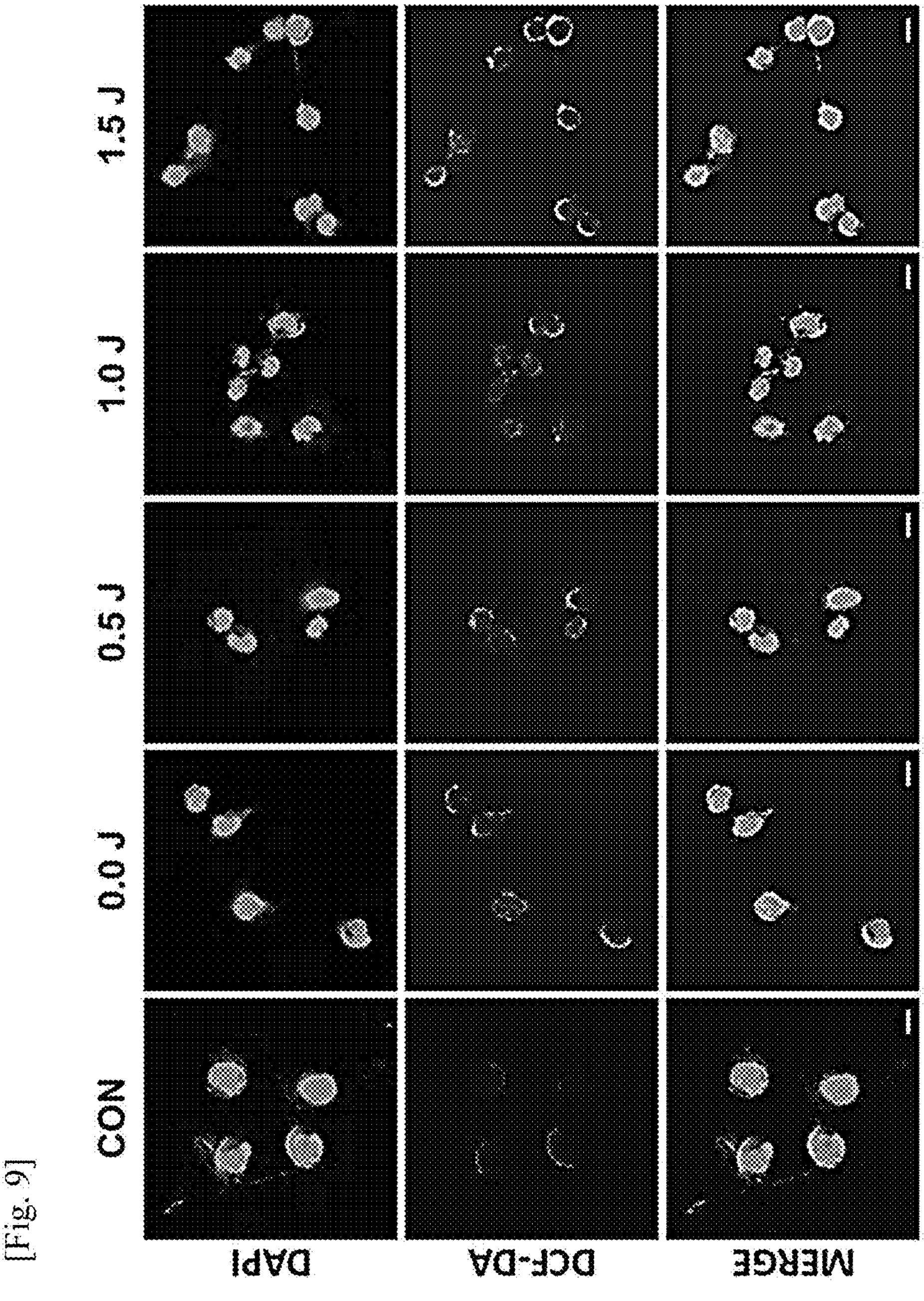

[Fig 10a]
HUTU-80
(GPR119 receptor +)
***
Cell Viability (%)
100
50
0
con 0.25 0.50 1.00 2.50 5.00 10.00
Ce6 Concentration (㎍/mL)
PC
PCL
OPC
OPCL
[Fig 10b]
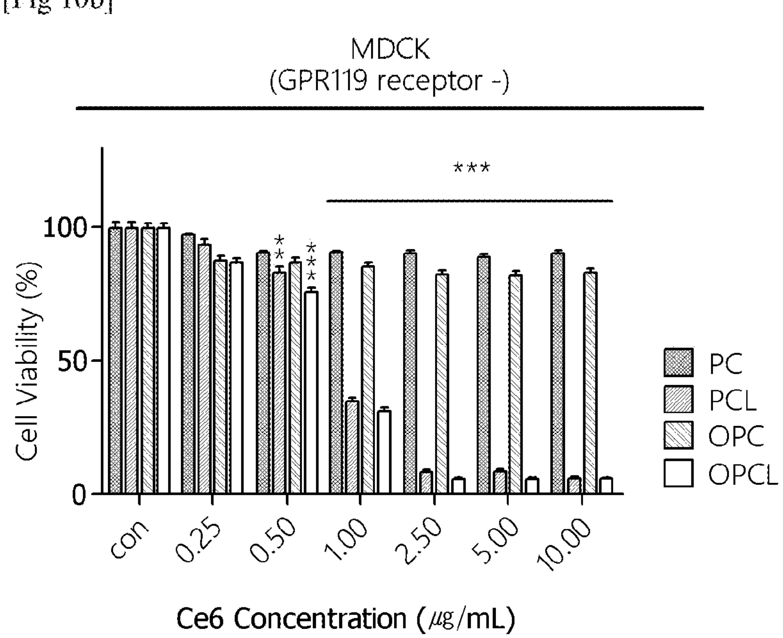

[Fig 11]
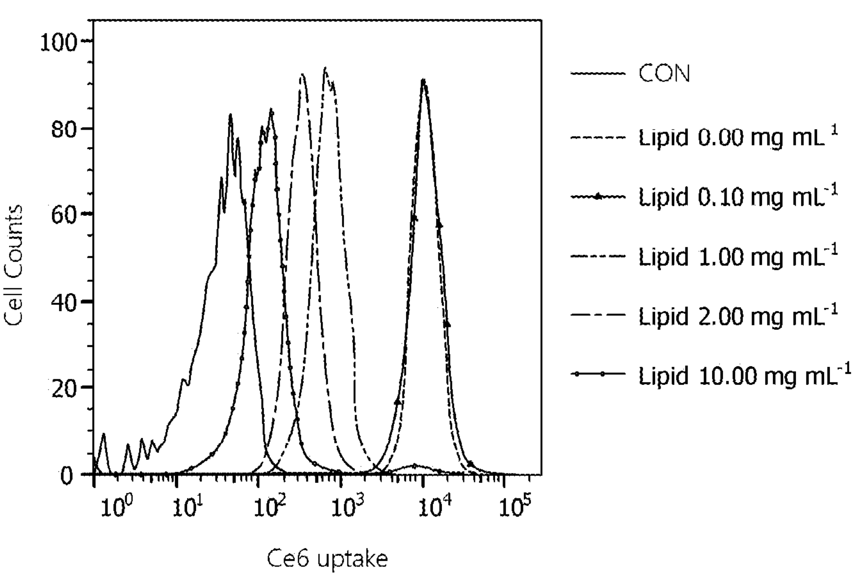
[Fig 12]
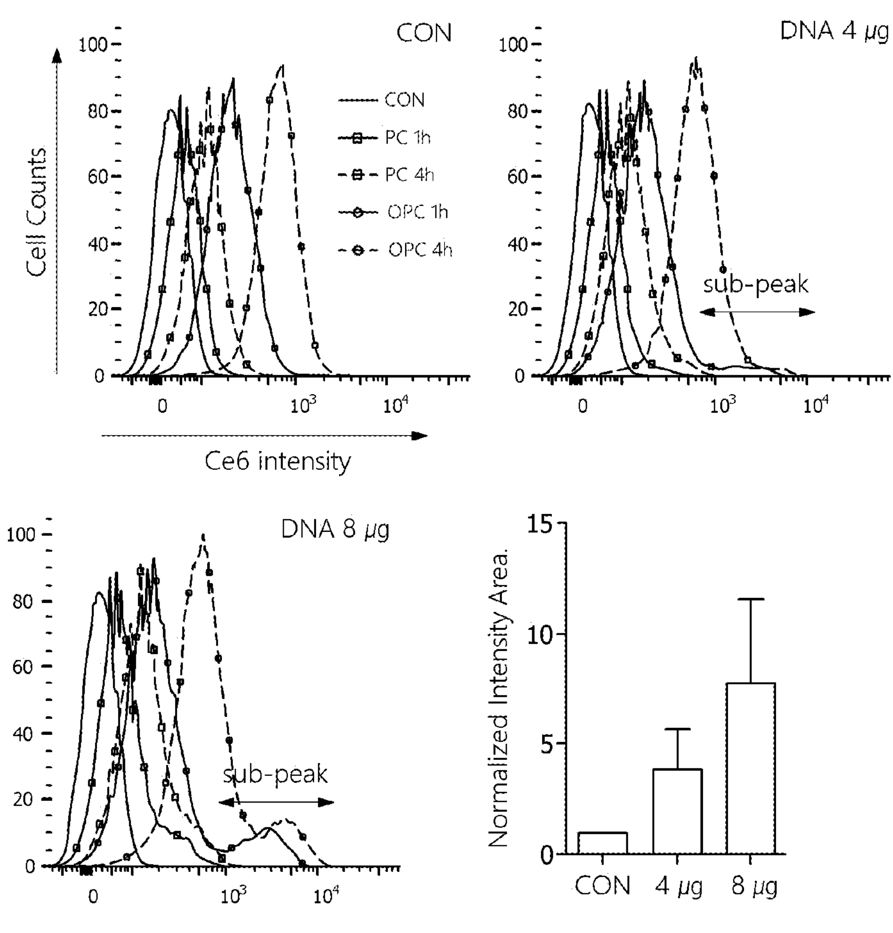

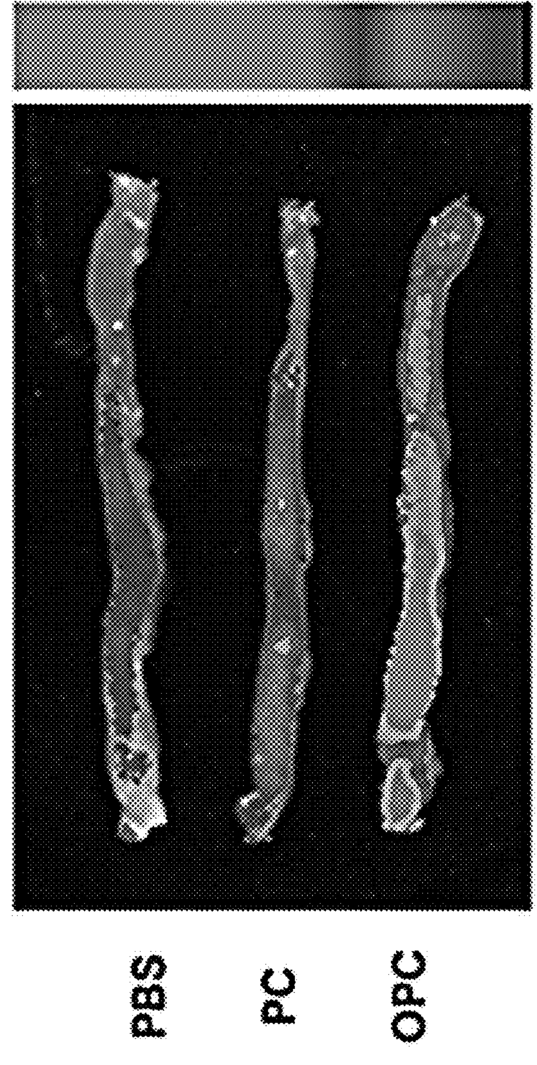
[Fig 13a]

[Fig 13b]
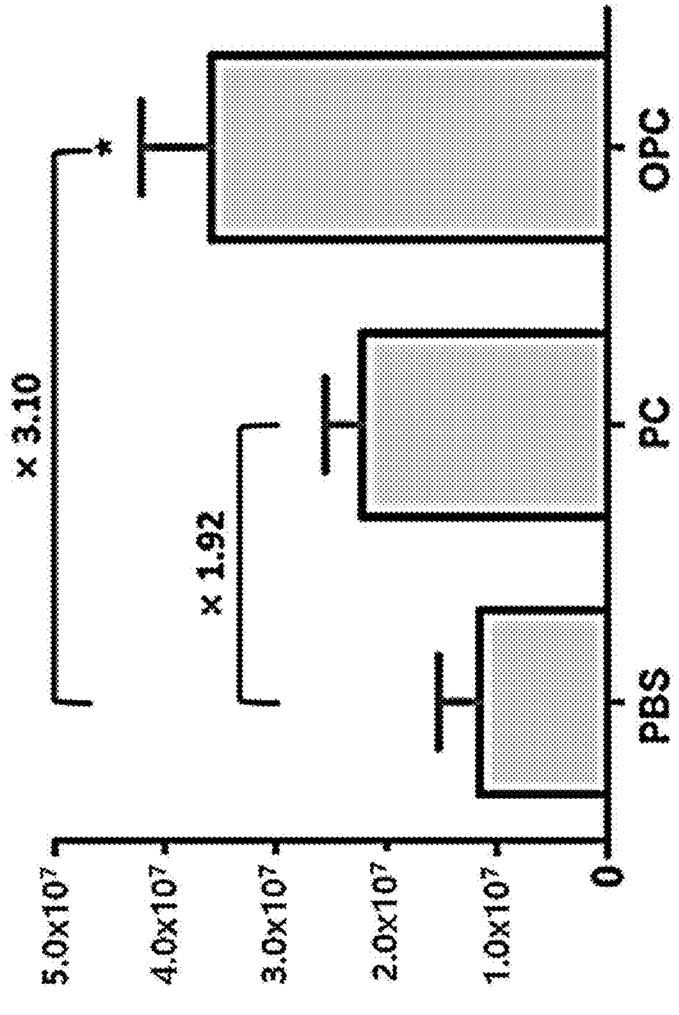

[Fig. 14a]
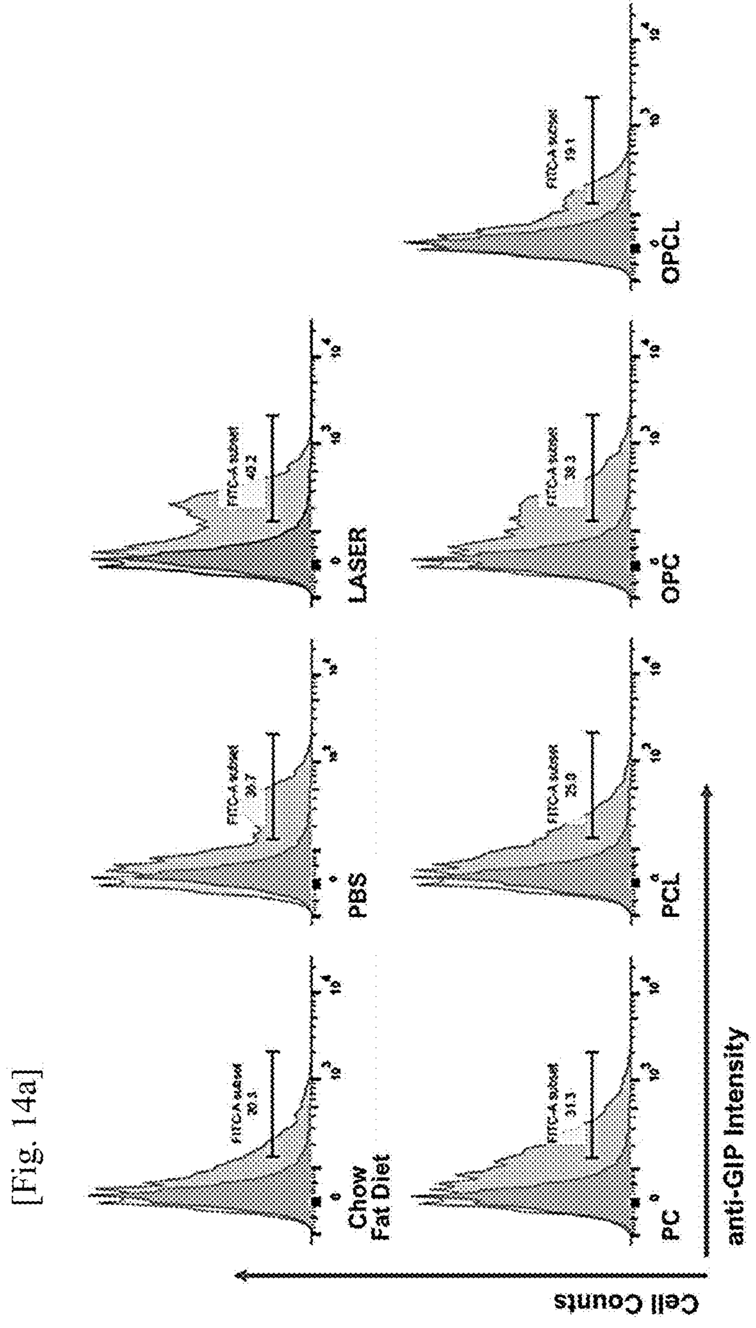

[Fig 14b]
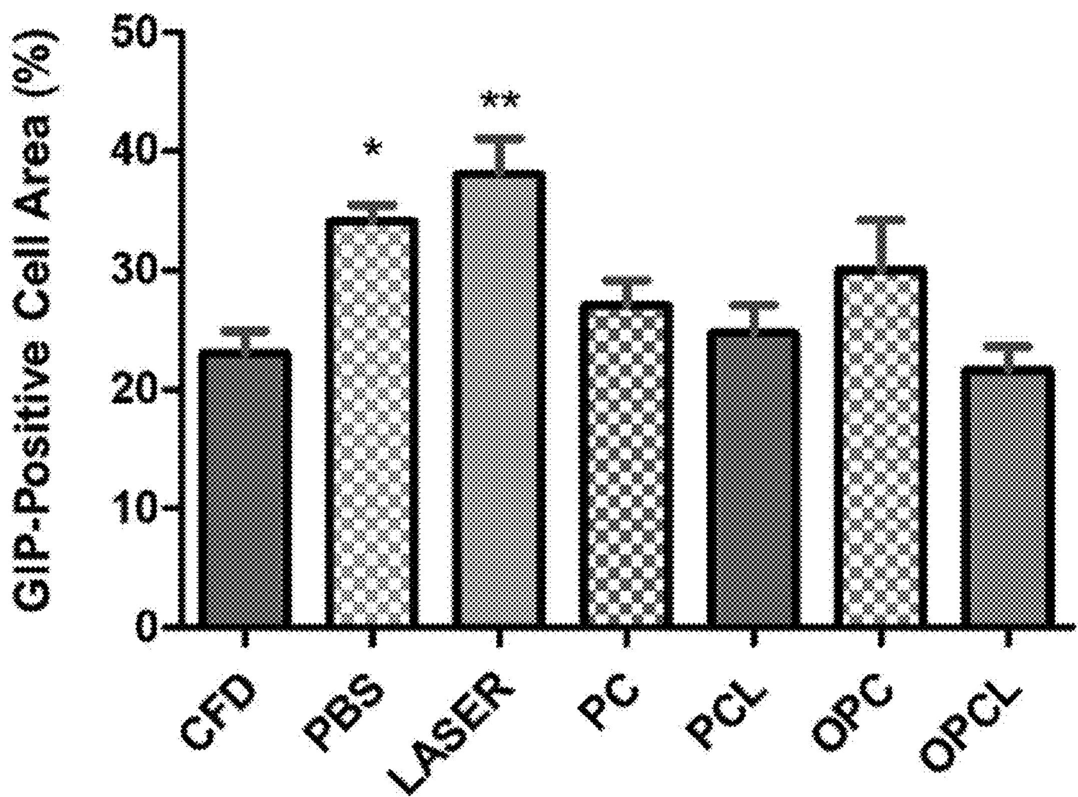

[Fig 15a]
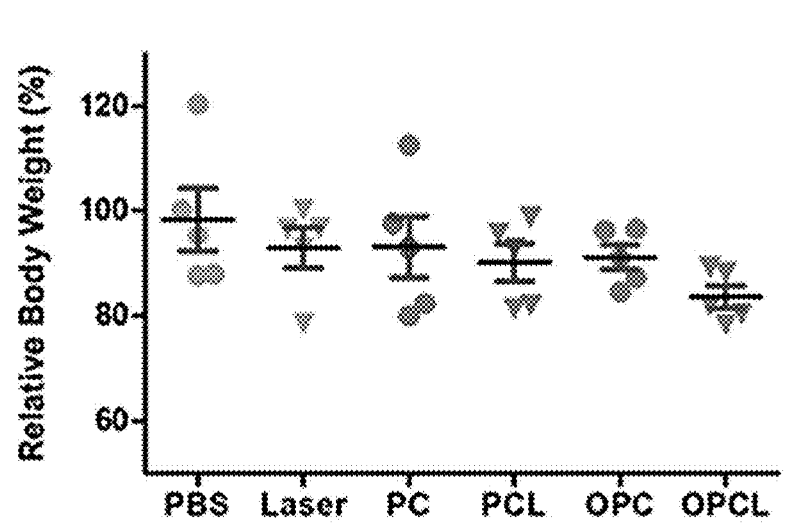
[Fig 15b]
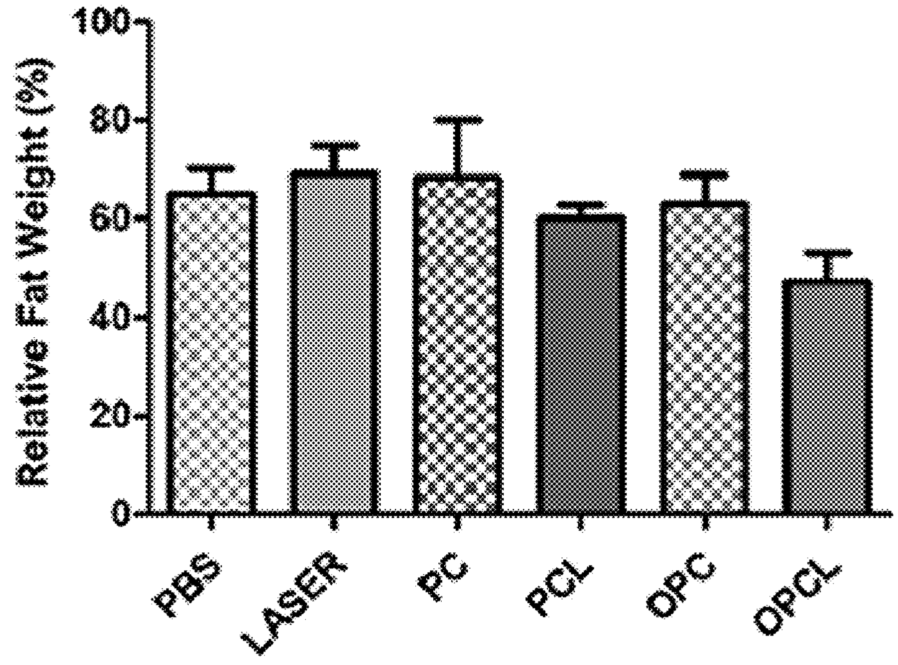

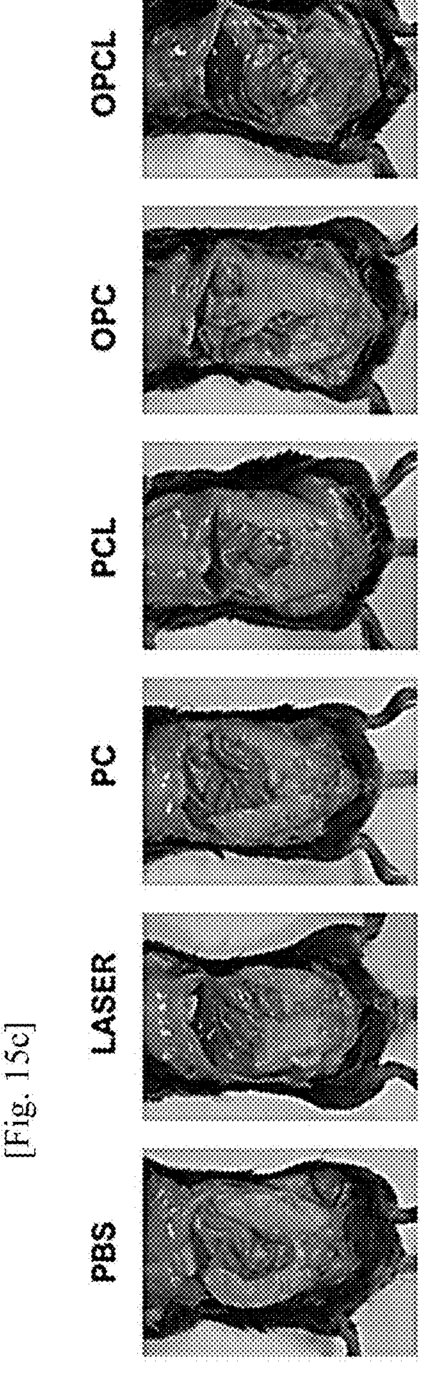
[Fig. 15c]

[Fig 16a]
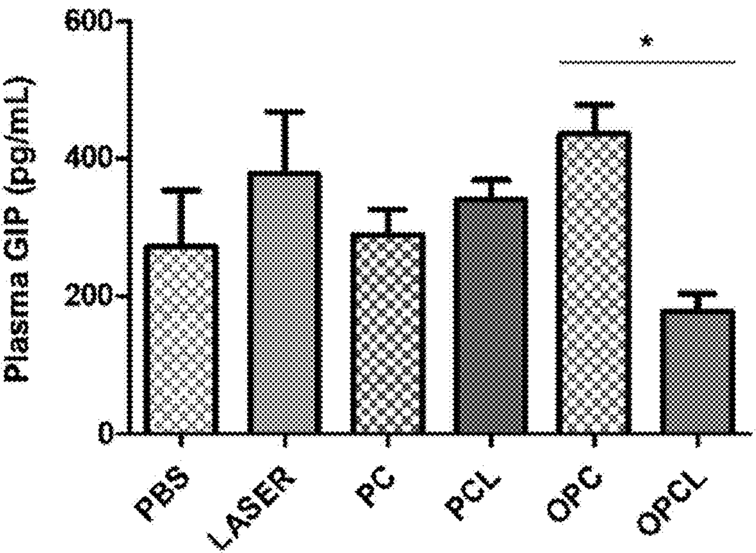
[Fig 16b]
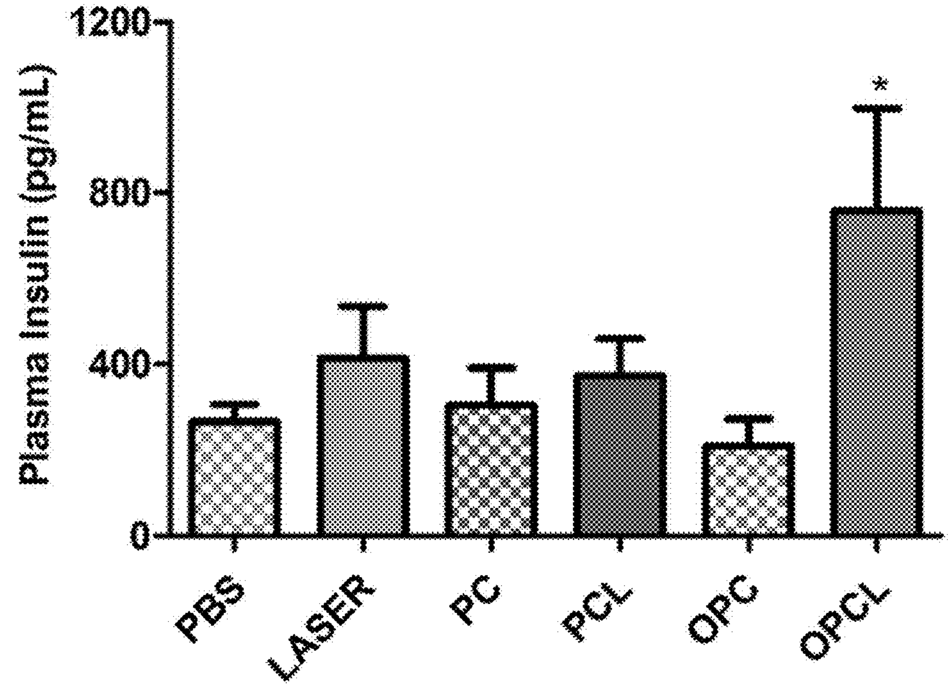

ENTEROENDOCRINE CELL-TARGETING POLYMER SUBSTANCE CONJUGATED WITH PHOTOSENSITIZER, AND MEDICAL USE THEREOF FOR AMELIORATING METABOLIC DISEASE

CROSS-REFERENCE TO RELATED APPLICATIONS

This application is a Section 371 of International Application No. PCT/KR2021/002830, filed Mar. 8, 2021, which was published in the Korean language on Nov. 25, 2021 under International Publication No. WO 2021/235661 A1, which claims priority under 35 U.S.C. § 119 (b) to Korean Application No. 10-2020-0060885, filed May 21, 2020, the disclosures of which are incorporated herein by reference in their entireties.

TECHNICAL FIELD

The present invention relates to a fatty acid-biocompatible polymer-photosensitizer conjugate and a composition for treating a metabolic disease, comprising the conjugate as an active ingredient.

BACKGROUND ART

Photodynamic therapy (PDT) is a medical treatment method using a photosensitizer, which is a photosensitive material. When a photosensitizer is irradiated with a laser of a specific wavelength, active oxygen is formed with ambient oxygen through a chemical reaction, and temporary disturbances due to oxidative stress is induced in surrounding cells or apoptosis is caused. When a photosensitizer is administered to a patient and selectively accumulated in cancer tissue after a certain period of time, the photosensitizer may be irradiated with a laser to induce the apoptosis of cancer cells. Although the existing photodynamic therapy was developed mainly for the purpose of treating tumors, extensive research is being conducted on bacteria, viruses, and the like including tumor cells, using an apoptosis mechanism. Accordingly, the target of diseases has expanded, so that applications are being made not only for cancer treatment, but also for the treatment of various diseases such as skin, eye, and viral diseases, and metabolic diseases.

Recently, the number of patients with obesity is rapidly increasing due to the westernization of dietary habits and changes in lifestyle. As of 2018, the obesity rate among adults aged 19 or more in Korea was about 34.8%, and the Organization for Economic Co-operation and Development (OECD) forecasts that the severely obese population will increase from 3.5% in 2005 and 5.3% in 2015 to 9.0% in 2030. Accordingly, public interest in severe obesity will be steadily increased. The risk of obesity is that there are many comorbidities that may develop from obesity. Patients with very severe obesity and obese patients with metabolic diseases cannot be reliably treated with diet therapy or chemical drugs alone, and bariatric metabolic surgery (jejunoileal bypass, adjustable gastric banding, Roux-en-Y gastric bypass, laparoscopic biliopancreatic diversion, sleeve gastrectomy, and the like) is primarily recommended to treat such patients. As bariatric metabolic surgery is covered by health insurance since Jan. 1, 2019, its domestic demand tends to increase. However, since bariatric metabolic surgery is a surgery that artificially changes the structure of organs, the surgery itself is very invasive, and side effects such as postoperative intestinal bleeding, thrombus formation, malnutrition and complications are enormous. Therefore, research into safer and simpler treatment methods capable of replacing bariatric metabolic surgery is required.

In addition, disease site diagnostic techniques using endoscopes and their accessories have recently been gradually developed. Optical transmission through an endoscope can provide direct access to diseased sites, enabling cancer diagnosis and treatment on a specific site. Further, combined with photodynamic therapy, it is possible to locate the position of a tumor by the fluorescence characteristics of a photosensitizer itself, and if a fluorescent site is irradiated with a laser, it is expected that the tumor cells will be killed by the generation of active oxygen. This is not limited to tumor cells, but can be applied as a method of modulating the activity of all cells present in the intestines and gastrointestinal tract.

As a result of conducting research on a non-invasive and effective method of treating obesity, the present inventors confirmed that when obesity- and diabetes-induced mice were orally administered a fatty acid-biocompatible polymer-photosensitizer conjugate and then irradiated with light, the blood GIP concentration was reduced, conversely, the insulin concentration was increased, and the body weight and fat weight were reduced to ameliorate the obese and diabetic conditions, thereby completing the present invention.

DISCLOSURE

Technical Problem

An object of the present invention is to provide a fatty acid-biocompatible polymer-photosensitizer conjugate and a use of the conjugate for ameliorating and treating metabolic diseases such as obesity and diabetes.

Technical Solution

To achieve the object, an aspect of the present invention provides a conjugate including: (a) a fatty acid; (b) a biocompatible polymer linked to the fatty acid via a covalent bond; and (c) a photosensitizer linked to the biocompatible polymer via a covalent bond.

In the present invention, the covalent bond may be selected from the group consisting of an amide bond, a carbonyl bond, an ester bond, a thioester bond and a sulfonamide bond.

In an exemplary embodiment of the present invention, the conjugate may be prepared by a method of first binding a fatty acid-biocompatible polymer and then further binding a photosensitizer, or binding a biocompatible polymer-photosensitizer and binding a fatty acid.

For example, an oleic acid-polyethylene glycol-chlorin e6 conjugate may be prepared using a polyethylene glycol having two amine groups as a biocompatible polymer. The conjugate may be prepared by reacting one amine group with a carboxyl group of oleic acid and reacting the amine group with a carboxyl group of chlorin e6.

In the present invention, the fatty acid may be selected from the group consisting of oleic acid, linoleic acid, palmitic acid, oleamide, oleoylethanolamide, palmitoylethanolamide, linoleyl ethanolamide, eicosenoic acid, arachidonic acid, lysophosphatidylserine, lysophosphatidic acid and oleoyldopamine, and may be preferably oleic acid.

The fatty acid allows the conjugate to be absorbed into enteroendocrine cells through the GPR119 receptor expressed in duodenal enteroendocrine cells. Therefore, the conjugate may target enteroendocrine cells such as K cells.

As used herein, the term "biocompatible polymer" refers to a material that is introduced in vivo and does not induce an adverse response such as an inflammatory response and/or an immune response, includes biodegradable and biostable materials, and serves as a linker that binds a fatty acid and a photosensitizer.

In the present invention, the biocompatible polymer may be selected from the group consisting of polyethylene glycol, glycol chitosan, pullulan, polyethyleneimine, chitosan, chitin, alginic acid, hydroxypropyl methylcellulose, dextrin, pectin, polyaniline, poly(ethylene glycol)bis(2-aminoethyl), poly(N-vinylpyrrolidone), poly-L-lysine, poly(4-vinylpyridine/divinylbenzene), poly(vinylamine) hydrochloride, poly (2-vinylpyridine), poly(2-vinylpyridine N-oxide), poly-ε-Cbz-L-lysine, poly(2-dimethylaminoethyl methacrylate), poly(allylamine) and poly(allylamine hydrochloride). Preferably, the biocompatible polymer may be polyethylene glycol, glycol chitosan, pullulan or polyethyleneimine, and may be most preferably polyethylene glycol.

In the present invention, the photosensitizer may be selected from the group consisting of chlorins, bacteriochlorins, phorphyrins, porphycenes and phthalocyanines. For example, meso tetra aminophenyl porphyrin, zinc protoporphyrin, protoporphyrin, and hemato porphyrin may be used as a phorphyrin-based photosensitizer, aluminum phthalocyanine may be used as a phthalocyanine-based photosensitizer, and chlorin e6 may be used as a chlorin-based photosensitizer.

In an exemplary embodiment of the present invention, the photosensitizer may be chlorin e6. Chlorin e6 is a hydrophobic material, but is linked to the biocompatible polymer via a covalent bond to increase hydrophilicity.

Another aspect of the present invention provides a pharmaceutical composition for preventing or treating a metabolic disease, including the conjugate as an active ingredient.

As used herein, the term "metabolic disease" refers to a set of abnormal conditions such as increased body fat, elevated blood pressure, elevated blood sugar, and abnormal blood lipids, and is not a single disease, but a comprehensive disease caused by the combination of genetic predisposition and environmental factors such as dietary habits.

In the present invention, the metabolic disease may be selected from the group consisting of obesity, diabetes, fatty liver, hyperlipidemia and hyperglycemia, and may be preferably obesity or diabetes.

The "obesity" refers to a condition in which surplus energy increases the amount and number of adipocytes in the body, resulting in excessive accumulation of adipose tissue. When the obesity state persists, abnormalities occur in in vivo metabolic processes, so that one or more symptoms of insulin resistance, type 2 diabetes, hyperlipidemia, fatty liver, or inflammation may appear with obesity.

The pharmaceutical composition of the present invention may be used for photodynamic therapy by irradiation with light. For example, when a subject in need of treatment for obesity and/or diabetes is administered the pharmaceutical composition and then irradiated with light, the conjugate absorbed into enteroendocrine cells generates active oxygen, so that enteroendocrine cells may be killed, resulting in amelioration of obese and diabetic conditions.

In addition, the pharmaceutical composition may be used as an endoscopic photodynamic therapeutic agent. For example, obese and/or diabetic conditions may be ameliorated by spraying the pharmaceutical composition into the intestinal tract of a subject in need of treatment for obesity and/or diabetes by an endoscope, and irradiating the intestinal tract with light by an endoscope.

The pharmaceutical composition of the present invention may include a pharmaceutically acceptable carrier in addition to the active ingredient. In this case, the pharmaceutically acceptable carrier is typically used during formulation, and includes lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, mineral oil, and the like, but is not limited thereto. Furthermore, the pharmaceutically acceptable carrier may further include a lubricant, a wetting agent, a sweetening agent, a flavoring agent, an emulsifier, a suspending agent, a preservative, and the like in addition to the above ingredients.

The pharmaceutical composition of the present invention may be administered orally or parenterally (for example, intravenous, subcutaneous, intraperitoneal or applied topically) according to the desired method. When the active ingredient of the present invention is formulated into a preparation such as tablets, capsules, chewable tablets, a powder, a liquid, and a suspending agent for the purpose of oral administration, it is possible to include a binder such as arabic rubber, corn starch, microcrystalline cellulose or gelatin, an excipient such as calcium diphosphate or lactose, a disintegrant such as alginic acid, corn starch, or potato starch, a lubricant such as magnesium stearate, a sweetening agent such as sucrose or saccharin, and a flavoring agent such as peppermint, methyl salicylate, or a fruit flavor.

The pharmaceutical composition of the present invention is administered in a pharmaceutically effective amount. In the present invention, the 'pharmaceutically effective amount' refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and other factors well known in the medical field. The pharmaceutical composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by a person skilled in the art.

Another aspect of the present invention provides a method for treating a metabolic disease, the method including: administering the pharmaceutical composition for preventing or treating a metabolic disease to an individual in need of treatment. Details such as dosage and administration method are as described for the pharmaceutical composition.

Severe bariatric surgery (for example, jejunoileal bypass, adjustable gastric banding, Roux-en-Y gastric bypass, laparoscopic biliopancreatic diversion, sleeve gastrectomy, and the like) and duodenal resurfacing (treatment method that non-specifically destroys intestinal cells using radio frequency) used to treat obesity have a sense of great burden in surgery due to side effects caused by changes in anatomical structure. Severe bariatric surgery has side effects such as thrombus formation at a fusion site and food outflow, and duodenal resurfacing has intestinal perforation problems.

In order to solve these problems, the present inventors devised a conjugate that can specifically kill only K cells, which are cells that secrete GIP, and confirmed the potential for a minimally invasive therapy for treating obesity by combining the conjugate with photodynamic therapy.

In the present invention, among the incretin hormones (consisting of GLP-1 and GIP), GIP hormone regulation is set as the main therapeutic target. GIP hormone regulation has great significance in having a direction different from the existing therapy targeting GLP-1 regulation to address obese and diabetic diseases.

Existing obesity treatment methods inject GLP-1 analogues ex vivo or use drugs that suppress the activity of DPP-4, which is an enzyme that degrades GLP-1, in order to increase the in vivo concentration of GLP-1 which is critically involved in insulin secretion. However, this treatment method cannot be a fundamental treatment method because higher concentrations of drugs need to be used over time due to the development of tolerance and even high doses are ineffective when the use of higher concentrations of drugs is repeated. Therefore, as a fundamental treatment method, a method of reducing the stimulation received by K cells that secrete GIP and maximizing the stimulation to be received by L cells that secrete GLP-1 was used. Depending on positional conditions, cells are activated more and earlier by greasy food to increase the secretion amount of GIP, and it was intended to improve this principle by killing K cells.

Advantageous Effects

The fatty acid-biocompatible polymer-photosensitizer conjugate according to the present invention can target K cells, which are enteroendocrine cells distributed in the duodenum, and can kill K cells that secrete GIP by producing active oxygen upon irradiation with light. Since the GIP hormone induces a decrease in fat accumulation and insulin secretion in obese and diabetic patients, the death of K cells that secrete the GIP hormone ameliorates obese and diabetic conditions, and accordingly, the conjugate can be effectively used for ameliorating and treating metabolic diseases such as obesity and diabetes.

DESCRIPTION OF DRAWINGS

FIG. 1 schematically illustrates the mechanism of action and method of application of an enteroendocrine cell-targeting conjugate produced according to an exemplary embodiment of the present invention.

FIG. 2 shows a chemical schematic view of oleic acid-polyethylene glycol-chlorin e6, which is an enteroendocrine cell-targeting polymer substance produced according to an exemplary embodiment of the present invention and the 1H-NMR spectrum results confirming the conjugation thereof.

FIG. 3 shows a chemical schematic view of oleic acid-glycol chitosan-chlorin e6, which is an enteroendocrine cell-targeting polymer substance produced according to an exemplary embodiment of the present invention and the 1H-NMR spectrum results confirming the conjugation thereof.

FIG. 4 shows a chemical schematic view of oleic acid-pullulan-chlorin e6, which is an enteroendocrine cell-targeting polymer substance produced according to an exemplary embodiment of the present invention and the 1H-NMR spectrum results confirming the conjugation thereof.

FIG. 5 shows a chemical schematic view of oleic acid-polyethyleneimine-chlorin e6, which is an enteroendocrine cell-targeting polymer substance produced according to an exemplary embodiment of the present invention and the 1H-NMR spectrum results confirming the conjugation thereof.

FIG. 6 shows the MALDI-TOF spectrum results of oleic acid-polyethylene glycol-chlorin e6, polyethylene glycol-chlorin e6 and chlorin e6.

FIG. 7 shows the results of confirming the singlet oxygen generation ability of oleic acid-polyethylene glycol-chlorin e6 according to laser irradiation intensity.

FIG. 8A shows the results of confirming the degree of intracellular accumulation after treating human duodenum cells (HUTU-80) with oleic acid-polyethylene glycol-chlorin e6 (OA-PEG-Ce6, OPC).

FIG. 8B shows the intracellular distribution of oleic acid-polyethylene glycol-chlorin e6 and polyethylene glycol-chlorin e6 after treating human duodenum cells (HUTU-80) and canine kidney cells (MDCK) with oleic acid-polyethylene glycol-chlorin e6 and polyethylene glycol-chlorin e6.

FIG. 9 shows the results of confirming the amount of singlet oxygen produced according to laser irradiation intensity after treating human duodenum cells (HUTU-80) with oleic acid-polyethylene glycol-chlorin e6 (OA-PEG-Ce6, OPC).

FIG. 10A shows the results of confirming cytotoxicity and phototoxicity according to laser irradiation after treating human duodenum cells (HUTU-80) with oleic acid-polyethylene glycol-chlorin e6 (OA-PEG-Ce6, OPC).

FIG. 10B shows the results of confirming cytotoxicity and phototoxicity according to laser irradiation after treating canine kidney cells (MDCK) with oleic acid-polyethylene glycol-chlorin e6 (OA-PEG-Ce6, OPC).

FIG. 11 shows the results of confirming the competitive inhibitory effect by analyzing the degree of intracellular influx after treating human duodenum cells (HUTU-80) simultaneously with oleic acid-polyethylene glycol-chlorin e6 and excess oleic acid.

FIG. 12 shows the results of confirming the intracellular distribution of oleic acid-polyethylene glycol-chlorin e6 according to the expression level of GPR119 by expressing a GPR119 receptor in HEK-293 cells to implement a K cell-like cell model and treating HEK-293 cells with oleic acid-polyethylene glycol-chlorin e6.

FIG. 13 shows the results of confirming the degree of OPC accumulation in the duodenum after oral administration of oleic acid-polyethylene glycol-chlorin e6 (OPC) to obese and diabetic mouse models.

FIG. 14A shows the results of confirming, by a flow cytometer, that the amount of GIP is changed by orally administering oleic acid-polyethylene glycol-chlorin e6 (OPC) to obese and diabetic mouse models, then irradiating the models with a laser and removing duodenal enteroendocrine cells.

FIG. 14B graphically illustrates the results identified in FIG. 14A.

FIG. 15A shows the results of performing photodynamic therapy by orally administering oleic acid-polyethylene glycol-chlorin e6 (OPC) to obese and diabetic mouse models, and then irradiating the mouse models with a laser, and confirming the body weight of mice after 22 days.

FIG. 15B shows the results of performing photodynamic therapy by orally administering oleic acid-polyethylene glycol-chlorin e6 (OPC) to obese and diabetic mouse models, and then irradiating the mouse models with a laser, and confirming the changes in fat weight of mice after 22 days.

FIG. 15C shows the results of performing photodynamic therapy by orally administering oleic acid-polyethylene glycol-chlorin e6 (OPC) to obese and diabetic mouse models, and then irradiating the mouse models with a laser, and confirming the abdominal conditions of mice after 22 days.

FIG. 16A shows the results of performing photodynamic therapy by orally administering oleic acid-polyethylene glycol-chlorin e6 (OPC) to obese and diabetic mouse models, and then irradiating the mouse models with a laser, and analyzing the GIP concentration in the plasma of the mice after 22 days.

FIG. 16B shows the results of performing photodynamic therapy by orally administering oleic acid-polyethylene glycol-chlorin e6 (OPC) to obese and diabetic mouse models, and then irradiating the mouse models with a laser, and analyzing the insulin concentration in the plasma of the mice after 22 days.

MODE OF THE INVENTION

Hereinafter, one or more specific exemplary embodiments will be described in more detail through Examples. However, these Examples are provided only for exemplarily explaining the one or more specific exemplary embodiments, and the scope of the present invention is not limited to these Examples.

Preparation Example 1: Preparation of Enteroendocrine Cell-Targeting Substance Including Photosensitizer 1-1. Preparation of Photosensitizer Using Polyethylene Glycol as Linker A DCC/NHS catalytic reaction was used to bind chlorin e6 (Ce6) to polyethylene glycol diamine (PEG Mw 2 kDa) through an amide bond. 177.7 mg of Ce6, 74.3 mg of N—N'-dicyclohexycarbodiimide (DCC), and 41.4 mg of N-hydroxysuccinimide (NHS) were dissolved in 2 ml of dimethyformamide (DMF), and the resulting solution was stirred. After 4 hours, a solution was prepared by dissolving 500 ml of polyethylene glycol in 10 ml of separate dimethylformamide, and a solution of chlorin e6 activated in advance was added thereto, and the resulting solution was reacted at room temperature for 24 hours. After the reaction, the reaction product was dialyzed with primary distilled water for 3 days using a dialysis membrane (Spectra/Por; molecular weight cutoff size: 3500 Da) to remove the used solvent and catalyst. After the dialysis, the reaction product were lyophilized and collected in the form of a powder.

There are amine groups at both ends of polyethylene glycol, and purification was performed with a Sephadex LH20 hydrophobic chromatography column in order to obtain only a material in which chlorin e6 was conjugated to only one of these amine groups. The lyophilized powder was dissolved in methanol, the resulting solution was injected into the column, and the mobile phase was allowed to flow down by gravity using 50% methanol (5:5=methanol:water, flow rate: 0.5 ml/min). A single chlorin e6-conjugated compartment was collected from the separate compartments, methanol was removed by a rotary evaporator, and the residue was lyophilized to remove water. Thereafter, the presence or absence of conjugation of chlorin e6 was confirmed by nuclear magnetic resonance spectroscopy (1H-NMR) analysis.

In order to conjugate oleic acid (OA) to the synthesized polyethylene glycol-chlorin e6 (PEG-Ce6), oleic acid was first activated. 22.6 mg of oleic acid, 19.8 mg of N—N'-dicyclohexycarbodiimide (DCC), and 11 mg of N-hydroxysuccinimide (NHS) were dissolved in 2 ml of dimethyl sulfoxide (DMSO), and the resulting solution was stirred. After 4 hours, 100 mg of polyethylene glycol-chlorin e6 was dissolved in the dimethyl sulfoxide solution, and the resulting solution was reacted with the previously activated oleic acid solution for 24 hours. The reaction product was dialyzed with primary distilled water for 4 days using a dialysis membrane (Spectra/Por; molecular weight cutoff size: 3500 Da). After the dialysis, the reaction product was lyophilized and collected in the form of a powder, and the presence or absence of conjugation of oleic acid was confirmed by nuclear magnetic resonance spectrum (1H-NMR) analysis (FIG. 2).

In addition, in order to determine whether oleic acid is conjugated, the molecular weights of polyethylene glycol-chlorin e6 (PC) and oleic acid-polyethylene glycol-chlorin e6 (OPC) were measured using a MALDI TOF voyager DE-STR (Matrix-associated laser desorption time-of-flight mass spectrometer) (Applied Biosystems, USA) (FIG. 3).

1-2. Preparation of Photosensitizer Using Glycol Chitosan as Linker

To synthesize oleic acid-glycol chitosan-chlorin e6, chlorin e6 (Ce6) was first conjugated to glycol chitosan using the DCC/NHS catalytic reaction. Specifically, 14.5 mg of Ce6, 6 mg of N—N'-dicyclohexylcarbodiimide (DCC), and 3.4 mg of N-hydroxysuccinimide (NETS) were dissolved in 1 ml of dimethyl sulfoxide (DMSO), and the resulting solution was stirred. After 4 hours, a solution of chlorin e6 activated in advance was added to 9 ml of purified water in which 50 mg of glycol chitosan was dissolved, and the resulting mixture was reacted at room temperature for 24 hours. Thereafter, the reaction product was dialyzed with primary distilled water for 3 days using a dialysis membrane (Spectra/Por; molecular weight cutoff size: 3500 Da) to remove the used solvent and catalyst. After the dialysis, the reaction product were lyophilized and collected in the form of a powder.

Figure 4:
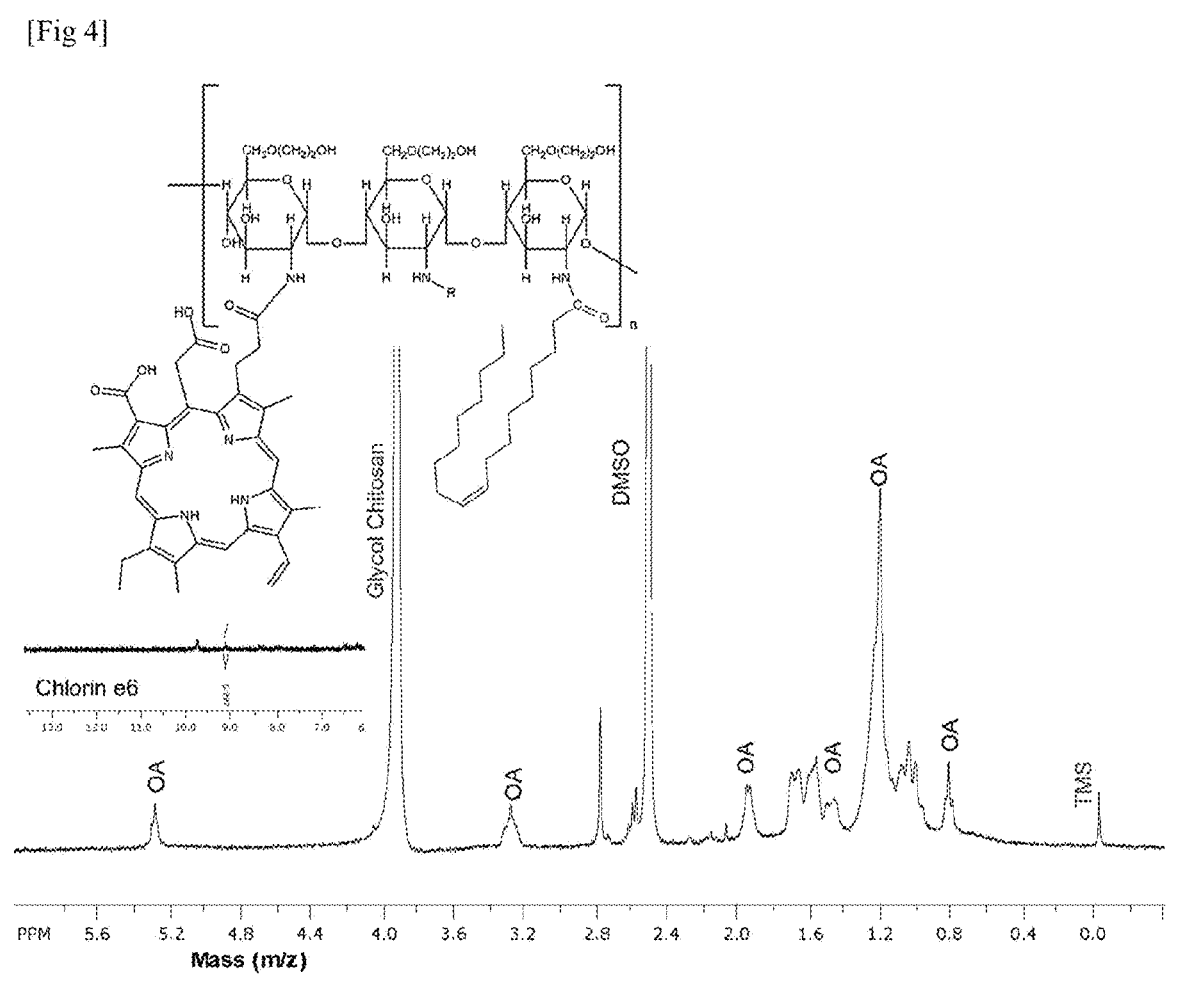

30 mg of glycol chitosan-chlorin, 46.17 μl of oleic acid, 36.2 mg of N-(3-dimethylaminopropyl)-N'-ethylcarbodiimide hydrochloride (EDC) and 20.2 mg of N-hydroxysuccinimide (NHS) were dissolved in 6 ml of dimethyl sulfoxide: purified (1:1), and the resulting solution was stirred for 48 hours. Thereafter, the reaction product was dialyzed with primary distilled water for 3 days using a dialysis membrane (Spectra/Por; molecular weight cutoff size: 3500 Da) to remove the used solvent and catalyst. After the dialysis, the reaction product was lyophilized and recovered in the form of a powder, and the presence or absence of conjugation of oleic acid was confirmed by nuclear magnetic resonance spectrum (1H-NMR) analysis (FIG. 4).

1-3. Preparation of Photosensitizer Using Pullulan as Linker

A DMAP/DCC catalytic reaction was used to bind oleic acid (OA) to pullulan (Mw 100 kDa) through an ester bond. 200 mg of pullulan, 165.2 mg of oleic acid, 144.8 mg of N—N'-dicyclohexylcarbodiimide (DCC), and 7.1 mg of 4-dimethylaminopyridine were added to 10 ml of dimethyl sulfoxide (DMSO), and the resulting solution was stirred for 48 hours. For purification, the solution was crystallized in 50 ml of diethyl ether, the supernatant other than the precipitate was discarded, and a process of performing recrystallization by again adding diethyl ether was repeated three times to remove unreacted substances and by-products. The resulting product was dried under reduced pressure and collected in the form of a powder, and the presence or absence of conjugation of oleic acid was confirmed by nuclear magnetic resonance spectrum (1H-NMR) analysis.

Figure 5:
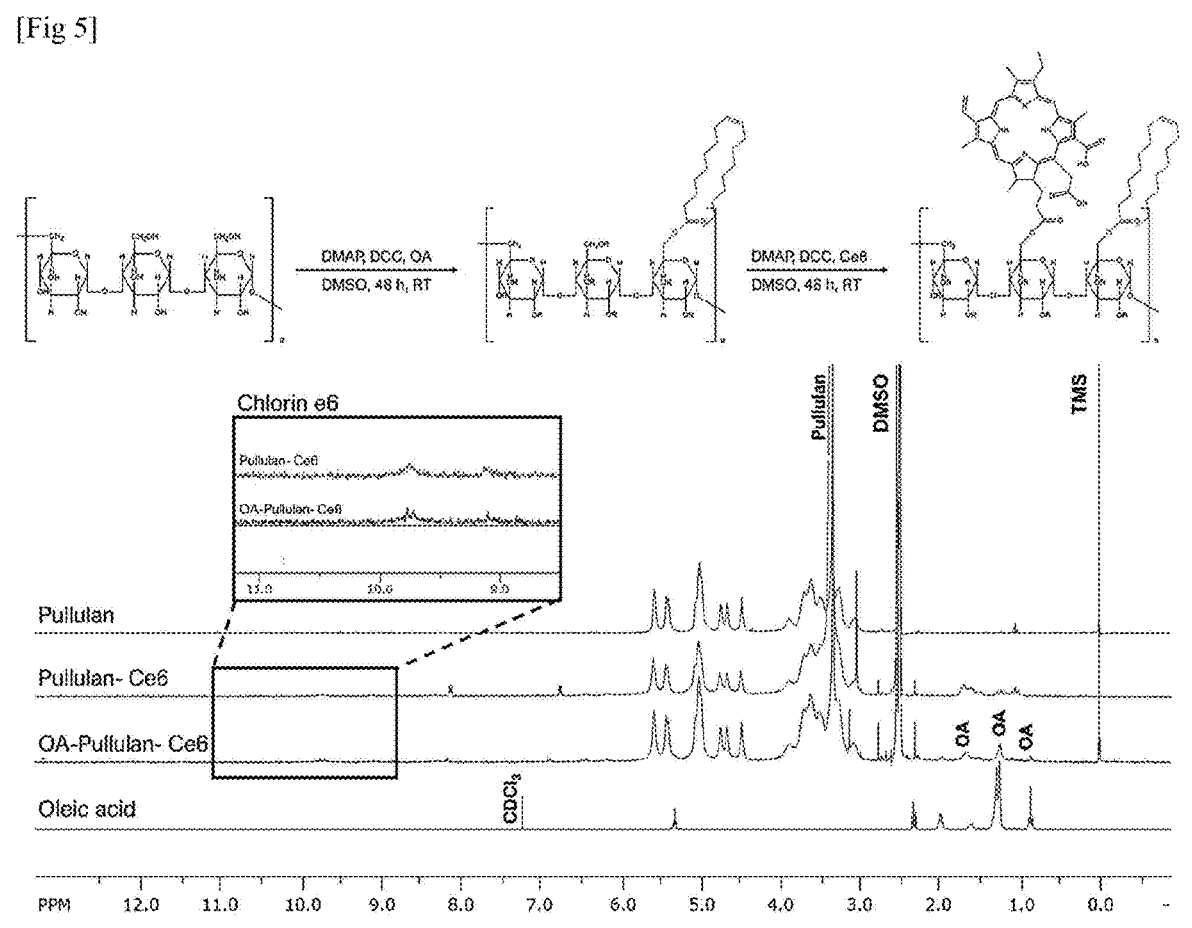

100 mg of oleic acid-pullulan, 64.8 mg of chlorin e6, 26.9 mg of N—N'-dicyclohexylcarbodiimide (DCC), and 1.3 mg of 4-dimethylaminopyridine were added to 10 ml of dimethyl sulfoxide (DMSO), and the resulting solution was stirred for 48 hours. For purification, the solution was crystallized in 50 ml of diethyl ether, the supernatant other than the precipitate was discarded, and a process of performing recrystallization by again adding diethyl ether was repeated three times to remove unreacted substances and by-products. The resulting product was dried under reduced pressure and collected in the form of a powder, and the presence or absence of conjugation of chlorin e6 was confirmed by nuclear magnetic resonance spectrum ($^1$H-NMR) analysis (FIG. 5).

1-4. Preparation of Photosensitizer Using Polyethyleneimine as Linker

A DCC/NHS catalytic reaction was used to bind oleic acid (OA) to polyethyleneimine (branched Mw 1800 D) through an amide bond. 2 ml of oleic acid, 1.570 g of N—N'-dicyclohexylcarbodiimide (DCC), and 0.8758 g of N-hydroxysuccinimide (NHS) were dissolved in 5 ml of dimethyl sulfoxide (DMSO), and the resulting solution was stirred. After 4 hours, a solution was prepared by dissolving 1 g of polyethyleneimine in 10 ml of dimethyl sulfoxide, and a solution of chlorin e6 activated in advance was added thereto, and the resulting solution was reacted at room temperature for 48 hours.

A DCC/NHS catalytic solution was used to bind chlorin e6 to oleic acid-polyethyleneimine through an amide bond. 135.56 mg of Ce6, 56.25 mg of N—N'-dicyclohexylcarbodiimide (DCC), and 31.38 mg of N-hydroxysuccinimide (NHS) were dissolved in 5 ml of dimethyl sulfoxide, and the resulting solution was stirred. After 4 hours, 100 mg of oleic acid-polyethyleneimine was dissolved in 5 ml of dimethyl sulfoxide, and the resulting solution was reacted with previously activated chlorin e6 for 48 hours. For purification, the reaction product was dialyzed with primary distilled water for 4 days using a dialysis membrane (Spectra/Por; molecular weight cutoff size: 3500 Da). After the dialysis, the reaction product was lyophilized and collected in the form of a powder, and the presence or absence of conjugation was confirmed by nuclear magnetic resonance spectrum ($^1$H-NMR) analysis (FIG. 6).

Experimental Example 1: Evaluation of Ability of Enteroendocrine Cell-Targeting Polymer to Form Active Oxygen The ability of the enteroendocrine cell-targeting polymer (oleic acid-polyethylene glycol-chlorin e6; hereinafter, described as OA-PEG-Ce6 or OPC) produced in Preparation Example 1 to form singlet oxygen was confirmed as follows.

Singlet oxygen sensor green (SOSG), which is a fluorescent detecting substance that directly reacts with singlet oxygen, was dispersed in an aqueous phase, oleic acid-polyethylene glycol-chlorin e6 (5 μg/mL) was added thereto, and the resulting mixture was mixed. As a comparative example, chlorin e6 (5 μg/mL) or polyethylene glycol-chlorin e6 (5 μg/mL) was used. When OA-PEG-Ce6 and SOSG coexisted in the aqueous phase, the mixture was irradiated with a laser (670 nm) (4 J/cm$^2$, 20 mW/cm$^2$, 200 seconds), and the degree of fluorescence was measured by an RF analyzer.

As a result of the measurement, it could be seen that the ability of OA-PEG-Ce6 to form active oxygen was similar to that of polyethylene glycol-chlorin e6 (PC), and it could be confirmed that chlorin e6 (freeCe6) could hardly form active oxygen (FIG. 7).

From the above results, it could be confirmed that chlorin e6 could not be dispersed in the aqueous phase due to its strong hydrophobic property, and thus could not form active oxygen, but polyethylene glycol-chlorin e6 and oleic acid-polyethylene glycol-chlorin e6 were well dispersed in water because hydrophilicity was increased due to the introduction of a hydrophilic polymer, thereby increasing the ability to form singlet oxygen.

Experimental Example 2: Confirmation of Intracellular Uptake of Enteroendocrine Cell-Targeting Polymer It was confirmed whether or not the OA-PEG-Ce6 produced in Preparation Example 1 flows into cells, particularly whether a large amount specifically flows into duodenal cells.

Human duodenal cells (HUTU-80) were aliquoted at a density of 1×10$^5$ cells/well in 2 ml portions in a 6-well cell culture dish and cultured under conditions of 37° C. and 5% $CO_2$ for 24 hours. Thereafter, the cells were treated with OA-PEG-Ce6 and polyethylene glycol-chlorin e6 as a comparative group at a concentration of 2 μg/ml (based on chlorin e6) for 1 hour and 4 hours, respectively. Thereafter, the cells were washed three times with DPBS, collected, and analyzed by a flow cytometer (BD FACSCanto II).

As a result of the analysis, it could be confirmed that OA-PEG-Ce6 (OPC) was more absorbed by the cells than polyethylene glycol-chlorin e6 (PC), and the longer the treatment time, the larger the amount absorbed (FIG. 8A).

Human duodenal cells (HUTU-80) and canine kidney epithelial cells (MDCK) were treated with OA-PEG-Ce6 and polyethylene glycol-chlorin e6 at a concentration of 2 μg/ml (based on chlorin e6) for 1 hour. Thereafter, the cells were washed three times with DPBS and fixed with 4% paraformaldehyde, and the cell nuclei were stained at 4° C. Thereafter, cell images were confirmed under a confocal laser scanning microscope (CLSM).

As a result of confirmation, it could be seen that OA-PEG-Ce6 (OPC) was more incorporated into cells than polyethylene glycol-chlorin e6 (PC) which targeting substance is free, and was more incorporated into human duodenal cells (HUTU-80) than in canine kidney epithelial cells (MDCK). In the images observed under the confocal microscope, blue indicates cell nuclei and red indicates chlorin e6 incorporated into cells (FIG. 8B).

Experimental Example 3: Evaluation of Ability of Enteroendocrine Cell-Targeting Polymer to Form Intracellular Active Oxygen After the OA-PEG-Ce6 produced in Preparation Example 1 was incorporated into cells, it was confirmed whether the OA-PEG-Ce6 could effectively form active oxygen and induce apoptosis when the cells were irradiated with a light.

Human duodenal cells (HUTU-80) were aliquoted at a density of 1×10$^5$ cells/well in 2 ml portions in each well of a 6-well plate containing glass and cultured under conditions of 37° C. and 5% $CO_2$ for 24 hours. Thereafter, the cells were treated with OA-PEG-Ce6 at a concentration of 2 μg/ml (based on chlorin e6) for 2 hours, and washed three times with DPBS. The cells were treated with DCFDA diluted in DPBS, cultured for 30 minutes, and further washed three times with DPBS. The cells were irradiated with a light with an intensity of 0, 0.5, 1 and 1.5 J/$cm^2$ to induce a reaction between DCFDA incorporated into the cells and singlet oxygen. Fluorescence appears when the two substances react. Thereafter, the cells were fixed with 4% paraformaldehyde, the cell nuclei were stained with DAPI, and images were confirmed under a confocal microscope.

As a result of confirmation, it could be confirmed that as the intensity of the light was increased, OA-PEG-Ce6 generated a large amount of active oxygen and the fluorescence intensity (green fluorescence) was increased (FIG. 9). This result means that when cells are treated with OA-PEG-Ce6 and irradiated with a light, apoptosis can be induced by active oxygen.

Experimental Example 4: Confirmation of Cytotoxicity of Enteroendocrine Cell-Targeting Polymer A concentration range in which OA-PEG-Ce6 produced in Preparation Example 1 did not exhibit cytotoxicity and a concentration range in which it exhibited phototoxicity when the cells were irradiated with a laser were compared to confirm its potential as a photodynamic therapeutic agent.

Human duodenal cells (HUTU-80) and canine kidney cells (MDCK) were aliquoted at a density of $1\times10^4$ cells/well in 0.2 ml portions in each well of a 96-well plate and cultured under conditions of 37° C. and 5% $CO_2$ for 24 hours. On the next day, each well was treated with OA-PEG-Ce6 or polyethylene glycol-chlorin e6 at a concentration of 0.25 to 10 μg/ml (based on chlorin e6), and the corresponding treatment was performed by dividing a light non-irradiation group and a light irradiation group (irradiated with a laser with a wavelength of 671 nm at an intensity of 2 J/$cm^2$). Thereafter, cell viability was confirmed by the MTT test method.

As a result of confirmation, it could be seen that neither OA-PEG-Ce6 nor polyethylene glycol-chlorin e6 had cytotoxicity because there was no change in the cell viability of canine kidney cells (MDCK) in the light non-irradiation group (PC and OPC in FIG. 10B). In contrast, it could be confirmed that human duodenal cells (HUTU-80) showed almost no change in cell viability by polyethylene glycol-chlorin e6 treatment (PC in FIG. 10A), but OA-PEG-Ce6 treatment at a concentration of 2.5 μg/ml or higher decreased cell viability (OPC in FIG. 10A).

In the case of the light irradiation group, the cell viability of the canine kidney cells (MDCK) was remarkably reduced when the cells were treated with OA-PEG-Ce6 and polyethylene glycol-chlorin e6 at a treatment concentration of 2.5 μg/ml or higher (PCL and OPCL in FIG. 10B). In HUTU-80, that is, duodenal cells, cell viability was decreased starting at a treatment concentration of 0.5 μg/ml and higher for OA-PEG-Ce6 and 2.5 μg/ml and higher for polyethylene glycol-chlorin e6 (PCL and OPCL in FIG. 10A).

From the above results, it was confirmed that when OA-PEG-Ce6 was irradiated with a light, more toxicity appeared in human duodenal cells (HUTU-80). Neither OA-PEG-Ce6 nor polyethylene glycol-chlorin e6 showed significant toxicity when the cells were not irradiated with the light. Therefore, it could be seen that the presence of oleic acid can induce duodenum-specific apoptosis.

Experimental Example 5: Confirmation of Competitive Inhibitory Effect of Enteroendocrine Cell-Targeting Polymer in Presence of Fatty Acid It was confirmed by a competitive inhibition experiment whether the ability of OA-PEG-Ce6 to target duodenal cells was due to fatty acids.

Human duodenal cells (HUTU-80) were aliquoted at a density of $1\times10^5$ cells/well in 2 ml portions in each well of a 6-well plate and cultured under conditions of 37° C. and 5% $CO_2$ for 24 hours.

Thereafter, the cells were treated with both 0.10 to 10.00 mg/ml oleylethanolamine and 10 μg/ml OA-PEG-Ce6 (based on chlorin e6) and cultured for 2 hours. Thereafter, the cells were washed three times with DPBS, collected, and analyzed by a flow cytometer (BD FACSCanto II).

As a result of quantitative analysis of the fluorescence intensity of the flow cytometer, it could be confirmed that the treatment concentration of oleylethanolamine increased, the fluorescence intensity of OA-PEG-Ce6 decreased, and thus intracellular uptake was reduced. These results mean that the ability of OA-PEG-Ce6 to be incorporated into duodenal cells is due to fatty acids (FIG. 11).

Experimental Example 6: Confirmation of Ability of Enteroendocrine Cell-Targeting Polymer to Recognize Fatty Acid According to Receptor Expression Level In order to confirm the mechanism by which OA-PEG-Ce6 targets enteroendocrine cells, human fetal kidney cells (HEK-293) expressing G protein-coupled receptor 119 (GPR119), which is a receptor known to recognize fatty acids, were produced.

HEK-293 cells were aliquoted at a density of $3\times10^5$ cells/well in 2 ml portions in a 6-well plate and cultured under conditions of 37° C. and 5% $CO_2$ for 24 hours. After 24 hours, a GPR119 expression vector (0, 4 and 8 μg) and polyethyleneimine (PEI) were added to a serum-free medium and mixed for 30 minutes so as to form a complex, and then each cell was treated with the complex for 4 hours. Thereafter, the medium was replaced with a medium containing bovine serum, and GPR119 was allowed to be expressed by culturing the cells for 48 hours. It was confirmed by western blotting whether GPR119 was expressed.

HEK-293 cells expressing GPR119 were treated with OA-PEG-Ce6 and polyethylene glycol-chlorin e6 as a comparative group at a concentration of 2 μg/ml (based on chlorin e6) for 1 hour and 4 hours, respectively. Thereafter, the cells were washed three times with DPBS, collected, and analyzed by a flow cytometer (BD FACSCanto II).

As a result of the analysis, it could be seen that the expression of GPR119 was increased as the GPR119 DNA treatment amount was increased, so the intracellular accumulation rate of OA-PEG-Ce6 was partially increased and the area of the sub-peak was also increased. As a result of converting the sub-peak fluorescence intensity into a bar graph, the group treated with 8 μg of DNA showed the highest value (FIG. 12). From these results, it could be confirmed that the ability of OA-PEG-Ce6 to target enteroendocrine cells is due to fatty acids-recognition receptors (for example, GPR119) expressed in the cells.

Experimental Example 7: Confirmation of Ability of Enteroendocrine Cell-Targeting Polymer to Regulate Hormones C57BL6 mice were fed a high-fat diet for 8 weeks to induce obese and diabetic conditions, and were divided into a control (PBS), a light irradiation group (Laser), a polyethylene glycol-chlorin e6 adiministration group (PC), a polyethylene glycol-chlorin e6 adiministration+light irradiation group (PCL), an OA-PEG-Ce6 adiministration group (OPC) and an OA-PEG-Ce6 adiministration+light sirradiation group (OPCL). Each group was orally administered the treated substance at a concentration of 10 mg/kg (based on chlorin e6), and after 30 minutes, a catheter was injected for endoscopic access and a laser was irradiated through the mouth. Thereafter, endocrine cells were isolated by removing the mouse duodenum, fixed with 4% paraformaldehyde, and then treated with Triton X-100 for 15 minutes to aid antibody permeation. The cells were bound to 1% bovine serum albumin (BSA) and treated with a gastric inhibitory peptide (GIP) antibody (1:200; ab22624, Abcam), which is a primary antibody, for 2 hours. The cells were washed three times with DPBS and treated with anti-rabbit IgG-FITC (1:200; A120-101D2, Bethyl), which is a secondary antibody, for 1 hour. Thereafter, the cells were analyzed by a flow cytometer (BD FACSCanto II).

As a result of the analysis, the GIP value was lowest in the normal group (chow fat diet, CFD) which ingested the general diet, and a high level of GIP was detected in the obesity-induced control (PBS). However, the OA-PEG-Ce6 adiministration+light irradiation group (OPCL) showed similar levels of GIP to the normal group (FIGS. 14A and 14B).

Meanwhile, the accumulation degree of photosensitizer in the removed duodenum was confirmed with a fluorescence-labeled organism bioimaging instrument (Neo Science), and the fluorescence intensity of each tissue was graphically shown. As a result of confirming the accumulation degree of photosensitizer in the polyethylene glycol-chlorin e6 adiministration group (PC) and the OA-PEG-Ce6 adiministration group (OPC), it could be confirmed that a remarkably large amount of photosensitizer was accumulated in the OA-PEG-Ce6 adiministration group (OPC) (FIG. 13).

The above results mean that when OA-PEG-Ce6 is administered to obese and diabetic mouse models and photodynamic therapy is performed, GIP secretion can be lowered by killing K cells, which are duodenal enteroendocrine cells.

Experimental Example 8: Confirmation of Obesity Amelioration Effect of Enteroendocrine Cell-Targeting Polymer C57BL6 mice were fed a high-fat diet for 8 weeks to induce obese and diabetic conditions, and were divided into a control (PBS), a light irradiation group (Laser), a polyethylene glycol-chlorin e6 adiministration group (PC), a polyethylene glycol-chlorin e6 adiministration+light irradiation group (PCL), an OA-PEG-Ce6 adiministration group (OPC) and an OA-PEG-Ce6 adiministration+light irradiation group (OPCL). Each group was orally administered the treated substance at a concentration of 10 mg/kg (based on chlorin e6), and after 30 minutes, a catheter was injected for endoscopic access and a laser was irradiated through the mouth (0.7 J/cm$^2$ (23.33 mW/cm$^2$, 30 seconds)). After 4 days, photodynamic therapy was performed once again by the same method, and then, changes in body weight and fat mass were measured every other day for 22 days. The experimental results were shown in a bar graph by dividing the body weight and fat mass on the last day of the experiment by the body weight and fat mass before the photodynamic therapy and then converting the obtained values into percentages. Fat mass was measured with EchoMRI-500 (Echo MRI, Houston, TX).

As a result of confirmation, the body weight was shown to be 98.3% for the control (PBS), 92.9% for the light irradiation group (Laser), 93.1% for the polyethylene glycol-chlorin e6 adiministration group (PC), 90.1% for the polyethylene glycol-chlorin e6 adiministration+light irradiation group (PCL), 91.1% for the OA-PEG-Ce6 adiministration group (OPC), and 83.6% for the OA-PEG-Ce6 adiministration+light irradiation group (OPCL), thereby showing the highest reduction in body weight in the OA-PEG-Ce6 adiministration+light irradiation group (OPCL) (FIG. 15A).

The fat mass was shown to be 65.2% for the control (PBS), 69.4% for the light irradiation group (Laser), 68.4% for the polyethylene glycol-chlorin e6 administration group (PC), 60.0% for the polyethylene glycol-chlorin e6 administration+light irradiation group (PCL), 62.8% for the OA-PEG-Ce6 administration group (OPC), and 47.2% for the OA-PEG-Ce6 adiministration+light irradiation group (OPCL), thereby showing the highest reduction in fat mass in the OA-PEG-Ce6 adiministration+light irradiation group (OPCL) (FIG. 15B).

The above results mean that when OA-PEG-Ce6 is administered to obese and diabetic mouse models and photodynamic therapy is performed, the secretion of GIP is reduced due to the death of K cells, which are a type of enteroendocrine cell, so that it is possible to obtain an effect of decrease in body weight and decrease in fat mass.

Experimental Example 9: Confirmation of Diabetes Amelioration Effect of Enteroendocrine Cell-Targeting Polymer C57BL6 mice were fed a high-fat diet for 8 weeks to induce obese and diabetic conditions, and were divided into a control (PBS), a light irradiation group (Laser), a polyethylene glycol-chlorin e6 adiministration group (PC), a polyethylene glycol-chlorin e6 adiministration+light irradiation group (PCL), an OA-PEG-Ce6 adiministration group (OPC) and an OA-PEG-Ce6 adiministration+light irradiation group (OPCL). Each group was orally administered the treated substance at a concentration of 10 mg/kg (based on chlorin e6), and after 30 minutes, a catheter was injected for endoscopic access and a laser was irradiated through the mouth (0.7 J/cm$^2$ (23.33 mW/cm$^2$, 30 seconds)).). After 4 days, photodynamic therapy was performed once again by the same method, and then, mouse blood was collected after 22 days. Plasma was isolated from blood to measure the concentrations of GIP (Merk Millipore, USA) and insulin (anti-insulin+pro insulin antibody (10 μg/ml, ab8304, Abcam)) by enzyme-linked immunosorbent assay (ELISA).

As a result of the measurement, the GIP was shown to be 271.3 pg/ml for the control (PBS), 377.6 pg/ml for the light irradiation group (Laser), 289.1 pg/ml for the polyethylene glycol-chlorin e6 adiministration group (PC), 339.6 pg/ml for the polyethylene glycol-chlorin e6 adiministration+light irradiation group (PCL), 435.5 pg/ml for the OA-PEG-Ce6 adiministration group (OPC), and 177.7 pg/ml for the OA-PEG-Ce6 adiministration+light irradiation group (OPCL), thereby showing the lowest GIP concentration in the OA-PEG-Ce6 adiministration+light irradiation group (OPCL) (FIG. 16A).

Insulin was shown to be 265.5 pg/ml for the control (PBS), 414.3 pg/ml for the light irradiation group (Laser), 304.3 pg/ml for the polyethylene glycol-chlorin e6 administration group (PC), 374.3 pg/ml for the polyethylene glycol-chlorin e6 adiministration+light irradiation group (PCL), 210.5 pg/ml for the OA-PEG-Ce6 adiministration group (OPC), and 758.0 pg/ml for the OA-PEG-Ce6 adiministration+light irradiation group (OPCL), thereby showing the highest insulin concentration in the OA-PEG-Ce6 adiministration+light irradiation group (OPCL) (FIG. 16B).

From the above results, it was confirmed that when OA-PEG-Ce6 is administered to obese and diabetic mouse models and photodynamic therapy is performed, the secretion of GIP is reduced due to the death of K cells, so that there is an effect of increasing insulin.

The invention claimed is:

1. A method for treating a metabolic disease, comprising administering to an individual in need of treatment a conjugate comprising:

(a) oleic acid;

(b) a biocompatible polymer covalently linked to the oleic acid and selected from the group consisting of PEG, chitosan, and pullulan; and (c) a photosensitizer linked to the biocompatible polymer via a covalent bond.

2. The method of claim 1, wherein the metabolic disease is selected from the group consisting of obesity, diabetes, fatty liver, hyperlipidemia and hyperglycemia.

3. The method of claim 1, wherein the conjugate is used for photodynamic therapy by photoirradiation.

4. The method of claim 1, wherein the photosensitizer is selected from the group consisting of chlorins, bacteriochlorins, phorphyrins, porphycenes and phthalocyanines.

5. The method of claim 4, wherein the chlorin photosensitizer is chlorin e6.

* * * * *